United States Patent
Tamegai (10) Patent No.: US 7,127,030 B2
(45) Date of Patent: Oct. 24, 2006

(54) AREA EXPOSURE DOSIMETRY AND AREA ABSORBED DOSIMETRY

(75) Inventor: Masahiro Tamegai, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/270,232

(22) Filed: Nov. 8, 2005

(65) Prior Publication Data

US 2006/0056592 A1   Mar. 16, 2006

Related U.S. Application Data

(63) Continuation of application No. 10/634,052, filed on Aug. 4, 2003.

(30) Foreign Application Priority Data

Aug. 5, 2002   (JP) .............................. 2002-228022

(51) Int. Cl.
*H05G 1/42* (2006.01)
(52) U.S. Cl. ........................................ 378/97; 378/108
(58) Field of Classification Search ............... 378/98.8, 378/98.7, 97, 108, 64, 95, 115
See application file for complete search history.

(56) References Cited

U.S. PATENT DOCUMENTS 6,047,042 A    4/2000  Khutoryansky et al. ...... 378/62
6,422,751 B1   7/2002  Aufrichtig et al. .......... 378/207
6,760,405 B1   7/2004  Ruetten et al. ............ 378/98.8
6,801,598 B1  10/2004  Tashiro et al. ............. 378/98.8
2004/0028182 A1* 2/2004  Tamegai .................... 378/98.7

FOREIGN PATENT DOCUMENTS

| JP | 10-052421   | 2/1998  |
| JP | 11-272851   | 10/1999 |
| JP | 3133741     | 2/2001  |
| JP | 2001-144932 | 5/2001  |
| JP | 2001-144966 | 5/2001  |

OTHER PUBLICATIONS

Dialog ABSTRACT for JP 10-052421.
Dialog ABSTRACT for JP 11-272851.
Dialog ABSTRACT for JP 3133741.
Dialog ABSTRACT for JP 2001-144966.
Dialog ABSTRACT for JP 2001-144932.

* cited by examiner

*Primary Examiner*—Courtney Thomas
*Assistant Examiner*—Hoon Song
(74) *Attorney, Agent, or Firm*—Morgan & Finnegan, L.L.P.

(57) ABSTRACT

The area of an irradiation region, and at least one of the area of an object region and the area of a non-object region in a radiation image obtained by radiographing an object are calculated. The effective dose of radiation from a radiation generator is acquired. An area exposure dose, the X-ray amount radiated on the object, is calculated on the basis of the area of the irradiation region, one of the area of the object region and the area of the non-object region, and an effective dose.

8 Claims, 12 Drawing Sheets

AREA EXPOSURE DOSIMETRY AND AREA ABSORBED DOSIMETRY

This is a continuation of co-pending application Ser. No. 10/634,052, filed Aug. 4, 2003.

FIELD OF THE INVENTION

The present invention relates to an area exposure dosimetry and area absorbed dosimetry.

BACKGROUND OF THE INVENTION

Recently, in practicing medical radiography, it is required to acquire and hold the exposure dose or absorbed dose of a patient as an area dose.

In order to meet this requirement, a method is used, in which an exit dosimeter (also called an area dosimeter) is placed near an X-ray source to measure an area radiation dose, and the measurement value is used as an area exposure dose. With this method, the area exposure dose of each patient is managed by a database.

It is, however, preferable not to use any exit dosimeter because it increases the cost of a radiography system. In accordance with such a market demand, a technique of predicting an area radiation dose from emission conditions (a tube current, tube voltage, emission time, and the like) and using the predicted dose as an area exposure dose has also been proposed. This method is disclosed in Japanese Patent No. 3133741.

Figure 12:
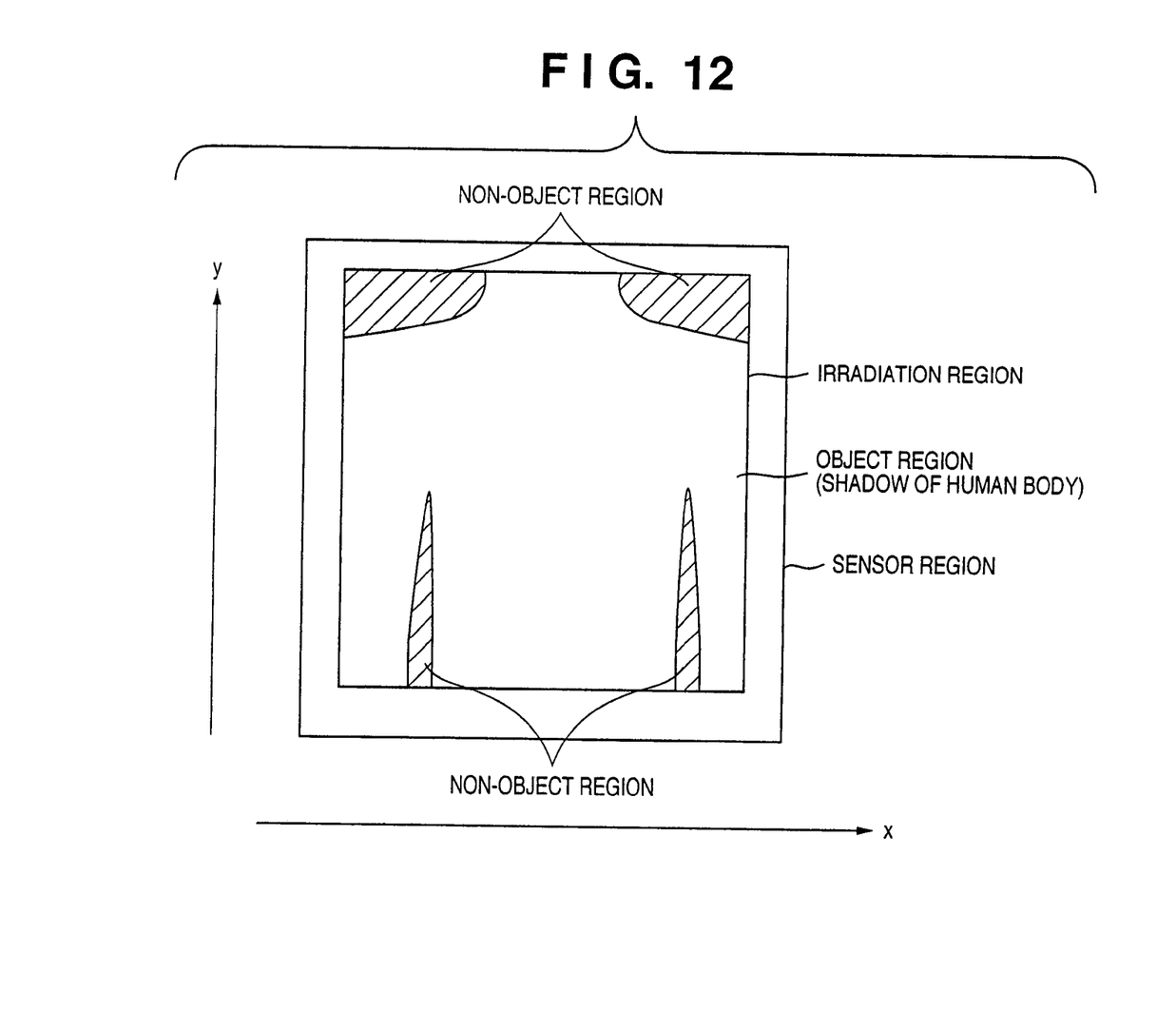
FIG. 12 is a conceptual view of an irradiation region, object region, and non-object regions.

On the other hand, recently, a digital radiography system has been increasingly used, in which elements for outputting electric charges in accordance with the amounts of X-rays received are arranged on a plane, and X-rays are captured as digital values to form a plane image. As disclosed in Japanese Patent Laid-Open Nos. 11-272851, 2001-144932, and 2001-144966, a digital radiography system can also recognize a region irradiated with X-rays (to be referred to as an "irradiation region" hereinafter) by scanning a captured image. X-rays transmitted through the human body become weaker than those which are not transmitted through the human body. This makes it possible to discriminate and recognize a region where X-rays are transmitted through the human body (to be referred to as an "object regions" hereinafter) and a region where the sensor is directly irradiated with X-rays (to be referred to as a "non-object region" hereinafter). This technique is also disclosed in the above references. FIG. 12 shows a conceptual view of an irradiation region, object region, and non-object regions.

Japanese Patent Laid-Open No. 10-52421 discloses a method of measuring the absorbed dose of a patient by using both an exit dosimeter and a digital radiography system. This method allows an operator to grasp the absorbed dose of a patient during radiography and can give a warning before irradiating the patient with excessive radiation.

In both the measuring method using a conventional exit dosimeter and the method of predicting a radiation dose from emission conditions and using the predicted value as the exposure dose of a patient, all the emitted X-rays are assumed to be transmitted through the human body, and are used as an exposure dose. In actual radiography, however, a region where no X-rays are transmitted through the human body (non-object region) may exist in even an irradiation region. In the presence of such a non-object region, the area radiation dose becomes higher than the actual area exposure dose of the human body. It is therefore inappropriate to use the area radiation dose as an area exposure dose without any change. Assume that a specified value of an area exposure dose is set, and radiography is inhibited above the specified value. In this case, since the held value exceeds the actual exposure dose, necessary radiography cannot be performed.

In radiographing the chest, in particular, since an X-ray image usually includes non-object regions, it is an urgent requirement to solve the above problem.

In the method of measuring the absorbed dose of a patient by using both a conventional exit dosimeter and a digital radiography system, two calibrations are required, including a calibration for the exit dosimeter and a calibration for the digital radiography system.

SUMMARY OF THE INVENTION

The present invention has been made in consideration of the above situation, and has as its object to properly acquire an area exposure dose and/or an area absorbed dose.

According to the present invention, the foregoing object is attained by providing an area exposure dosimetry method comprising: calculating an area of an irradiation region, and at least one of an area of an object region and an area of a non-object region in a radiation image obtained by radiographing an object; acquiring an effective dose of radiation from a radiation generator; and calculating an area exposure dose as a radiation dose of the object on the basis of the area of the irradiation region, the calculated one of the area of the object region and the area of the non-object region, and the effective dose.

According to the present invention, the foregoing object is attained by providing an area exposure dosimetry method comprising: recognizing a non-object region and an object region in a radiation image obtained by radiographing an object; calculating a unit area dose as a radiation dose per unit area of the non-object region on the basis of the radiation image; and calculating an area exposure dose as a radiation dose of the object on the basis of the unit area dose and the area of the object region.

Further, the foregoing object is also attained by providing an area absorbed dosimetry method comprising: recognizing an irradiation region and a non-object region in a radiation image obtained by radiographing an object; calculating a unit area dose as a radiation dose per unit area of the non-object region on the basis of the radiation image; and calculating an area absorbed dose as an absorbed radiation dose of the object on the basis of the unit area dose, the area of the irradiation region, and an overall image signal quantity of the radiation image.

Further, the foregoing object is also attained by providing an area exposure dosimetry apparatus comprising: an area calculating unit that calculates an area of an irradiation region, and at least one of an area of an object region and an area of a non-object region in a radiation image obtained by radiographing an object; an acquiring unit that acquires an effective dose of radiation from a radiation generator; and a dose calculating unit that calculates an area exposure dose as a radiation dose of the object on the basis of the area of the irradiation region, the calculated one of the area of the object region or the area of the non-object region, and the effective dose.

Further, the foregoing object is also attained by providing an area exposure dosimetry apparatus Comprising: an area recognizing unit that recognizes a non-object region and an object region in a radiation image obtained by radiographing an object; a unit area dose calculating unit that calculates a unit area dose as a radiation dose per unit area of the non-object region on the basis of the radiation image; and a dose calculating unit that calculates an area exposure dose as a radiation dose of the object on the basis of the unit area dose and the area of the object region.

Further, the foregoing object is also attained by providing an area absorbed dosimetry apparatus comprising: a region recognizing unit that recognizes an irradiation region and a non-object region in a radiation image obtained by radiographing an object; a unit area dose calculating unit that calculates a unit area dose as a radiation dose per unit area of the non-object region on the basis of the radiation image; and a dose calculating unit that calculates an area absorbed dose as an absorbed radiation dose of the object on the basis of the unit area dose, the area of the irradiation region, and an overall image signal quantity of the radiation image.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

Preferred embodiments of the present invention will be described in detail in accordance with the accompanying drawings.

<First Embodiment>

Figure 1:
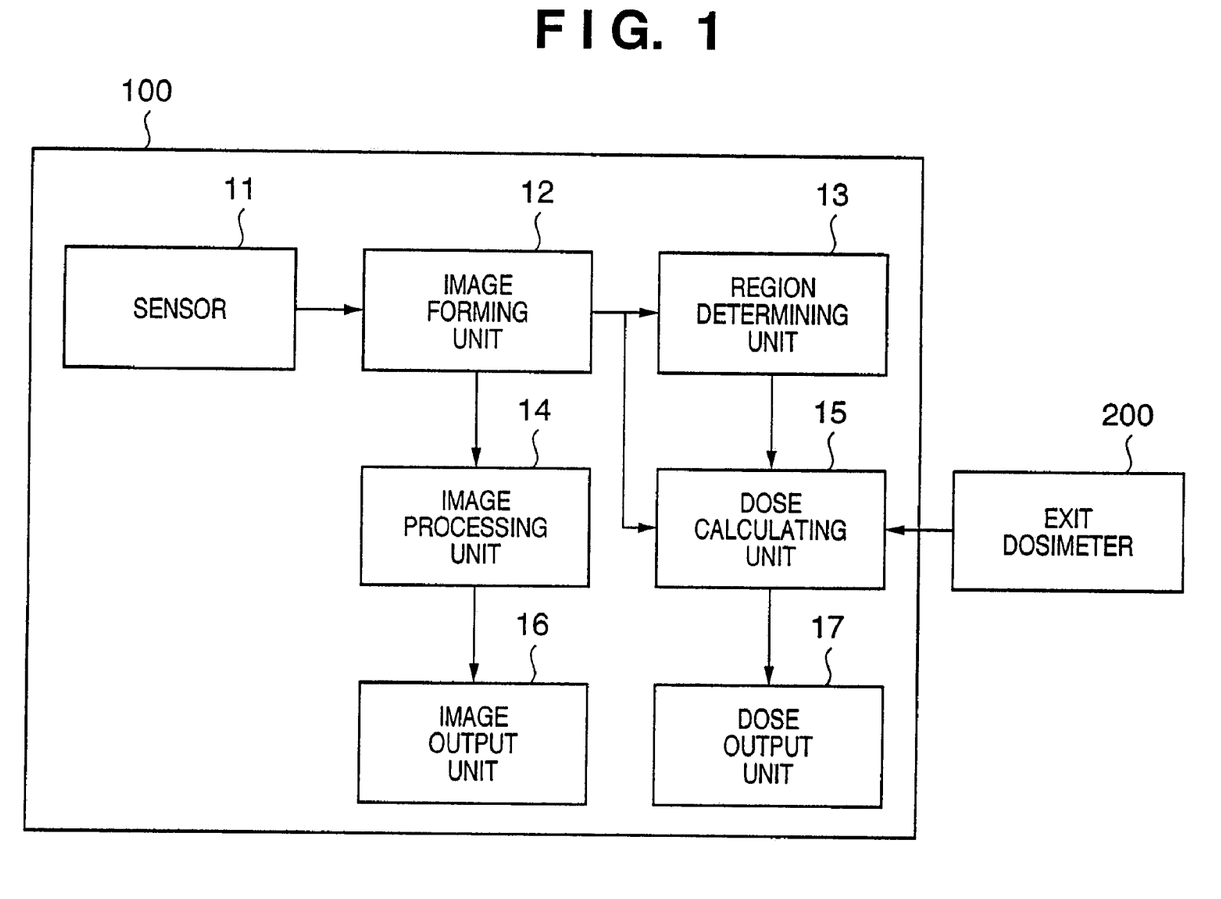
FIG. 1 is a block diagram showing the arrangement of an area exposure dosimetry system according to a first embodiment of the present invention.

FIG. 1 is a block diagram showing the arrangement of an exposure dosimetry system according to the first embodiment of the present invention. The exposure dosimetry system of the first embodiment includes a digital radiography system 100 and an exit dosimeter (to be also referred to as an area dosimeter) 200 which is placed on the side of the sensor with respect to an X-ray stop and measures the area dose of X-rays emitted.

In the digital radiography system 100, reference numeral 11 denotes a sensor obtained by arranging, on a plane, elements for generating electric charges in accordance with the intensity of X-rays; 12, an image forming unit which forms an image by collecting electric charge quantities from the respective elements of the sensor 11; 13, a region determining unit which scans the image output from the image forming unit 12 and determines an X-ray irradiation region, non-object region, and object region; 14, an image processing unit which changes the image output from the image forming unit 12 into an image which is easy for an operator to interpret; 15, a dose calculating unit which calculates the area exposure dose of a patient by using the image output from the image forming unit 12, the information output from the region determining unit 13, and the area dose value acquired from the exit dosimeter 200; 16, an image output unit which outputs the image processed by the image processing unit 14 to a PACS (Picture Archiving and Communication System) or the like; and 17, a dose output unit which outputs the area exposure dose calculated by the dose calculating unit 15 to, for example, an internal or external storage device and/or a display device. Of the components of the digital radiography system 100, the region determining unit 13, image processing unit 14, dose calculating unit 15, image output unit 16, and dose output unit 17 may be implemented by using a general-purpose personal computer and the like. The above PACS is a computer for storing digital images obtained by radiography.

Figure 2:
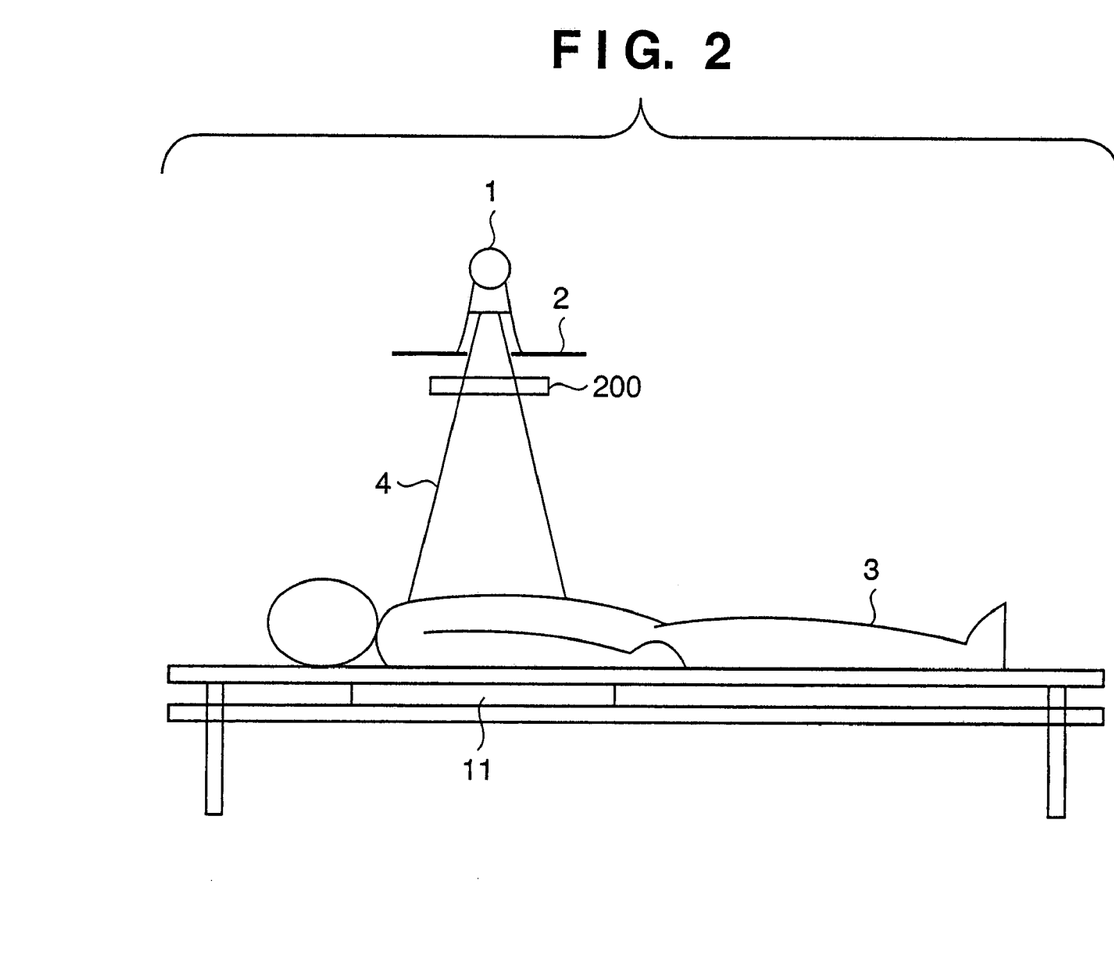
FIG. 2 is a view for explaining an outline of an radiography method according to the first embodiment of the present invention.

FIG. 2 is a view for explaining an outline of a radiography method according to the first embodiment of the present invention. The same reference numerals as in FIG. 1 denote the same parts in FIG. 2, and a description thereof will be omitted. Referring to FIG. 2, reference numeral 1 denotes an X-ray generator; 2, a radiation field stop for irradiating a limited portion of the human body with X-rays output from the X-ray generator 1; 3, a human body as an object with which X-rays are irradiated; and 4, X-rays. The exit dosimeter 200 measures the area dose of X-rays limited by the radiation field stop 2.

The irradiation region of the X-rays 4 emitted from the X-ray generator 1 is limited by the radiation field stop 2. The resultant area dose of X-rays is measured by the exit dosimeter 200. The human body 3 is then irradiated with the X-rays 4. Both X-rays which are transmitted through the human body 3 and those which are not transmitted therethrough are incident on the sensor 11 to be converted into electric charges corresponding to the amounts of incident X-rays. These electric charges are then used for the formation of a radiation digital image by the image forming unit 12.

Figure 3:
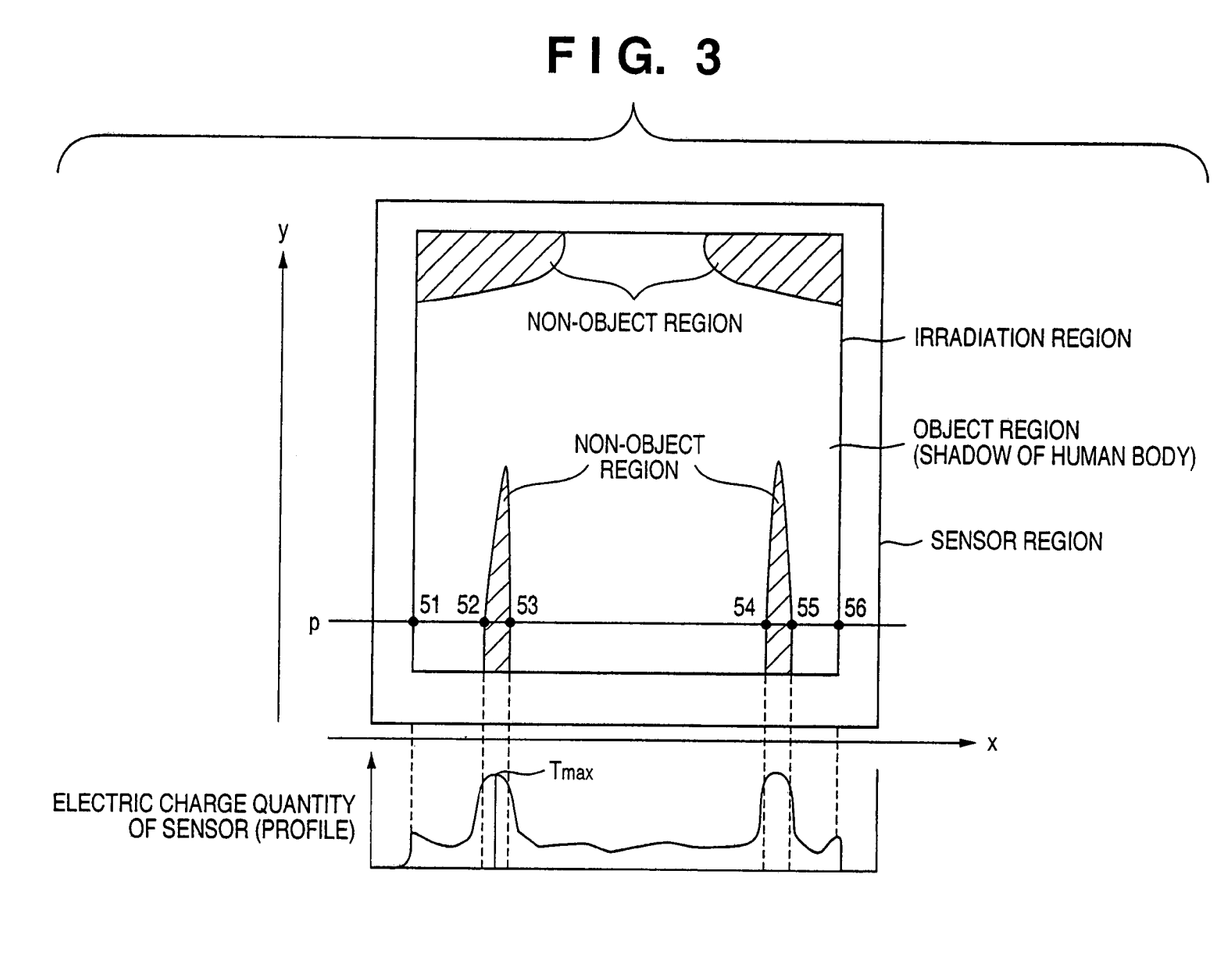
FIG. 3 is a view for explaining a method of discriminating an irradiation region and non-object regions according to the first embodiment of the present invention.

FIG. 3 is a view showing a method of recognizing an entire region irradiated with X-rays (to be referred to as an "irradiation region" hereinafter) and a region where the sensor 11 is directly irradiated with the X-rays 4 (to be referred to as a "non-object region" hereinafter) in a radiation digital image obtained in the above manner.

As shown in FIG. 3, the region determining unit 13 detects a horizontal profile at an arbitrary position p on the radiation digital image, and pays attention to positions where signal levels of elements of the sensor 11 change to levels equal to or higher than a threshold. In the case shown in FIG. 3, points 51 to 56 are points where the level of the profile abruptly changes. Of these points, the points 51 and 56 where the signal levels are close to 0 are determined as contour points of a radiation field, and the points 52 to 55 where the signal levels are close to the maximum level (Tmax) are determined as contour points of a region wherein X-rays are transmitted through the human body (to be referred to as an "object region" hereinafter). Subsequently, the same processing is performed at predetermined intervals in the vertical-direction, and the respective contour points are connected to each other to determine an irradiation region and non-object region.

A method of calculating an area exposure dose in the first embodiment of the present invention will be described below with reference to FIGS. 1 to 5.

Figure 4:
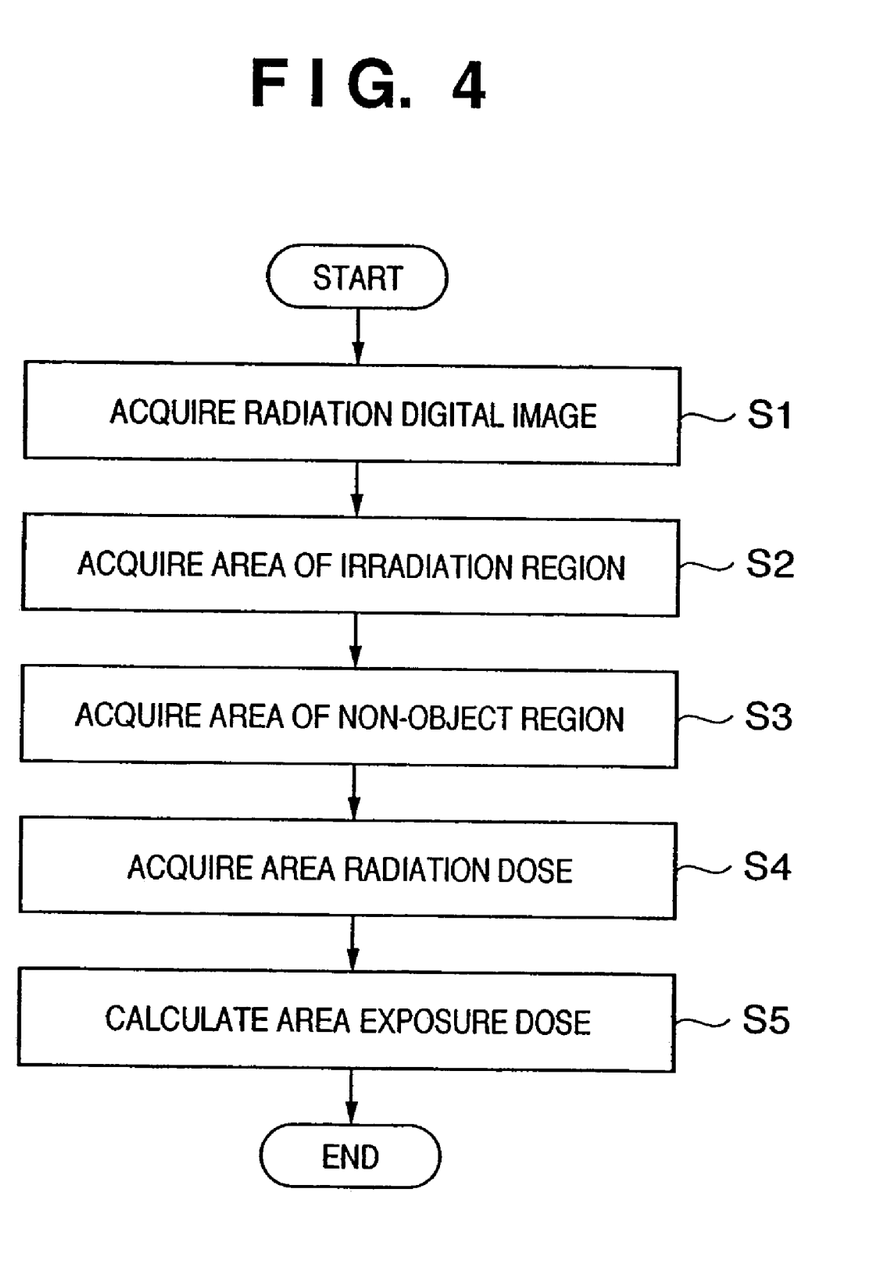
FIG. 4 is a flow chart showing the flow of processing for area exposure dose calculation according to the first embodiment according to the present invention.

FIG. 4 is a flow chart showing the flow of processing for area exposure dose calculation. In step SI, as described above, after the human body 3 is irradiated with the X-rays 4, the image forming unit 12 acquires data from the sensor 11 on an element (pixel) basis to form a radiation digital image. The region determining unit 13 calculates an area Sa of the irradiation region by the method described with reference to FIG. 3 in accordance with the information of the image forming unit. 12 (step S2). The region determining unit 13 further calculates an area Ss of a non-object region (step S3). The dose calculating unit 15 acquires an area radiation dose from the exit dosimeter 200 (step S4). Lastly, the dose calculating unit 15 calculates an area exposure dose.(step S5).

Processing for area exposure dose calculation in step S5 in FIG. 4 in the first embodiment will be described in detail next with reference to FIG. 5.

If it is determined in step S100 that the area Ss of the non-object region is 0, the area radiation dose acquired from the exit dosimeter 200 is transmitted as the area exposure dose of the human body to the dose output unit 17 (step S101). In contrast, if it is determined in step S100 that the area of the non-object region is not 0, an area exposure dose is calculated by using the area radiation dose acquired from the exit dosimeter 200 and the information received from the region determining unit 13 and is transmitted to the dose output unit 17 (step S102). In this case, letting M be the area radiation dose value received from the exit dosimeter 200, the area exposure dose is given by $$\text{area radiation dose} = M*(Sa-Ss)/Sa \quad (1)$$

Figure 5:
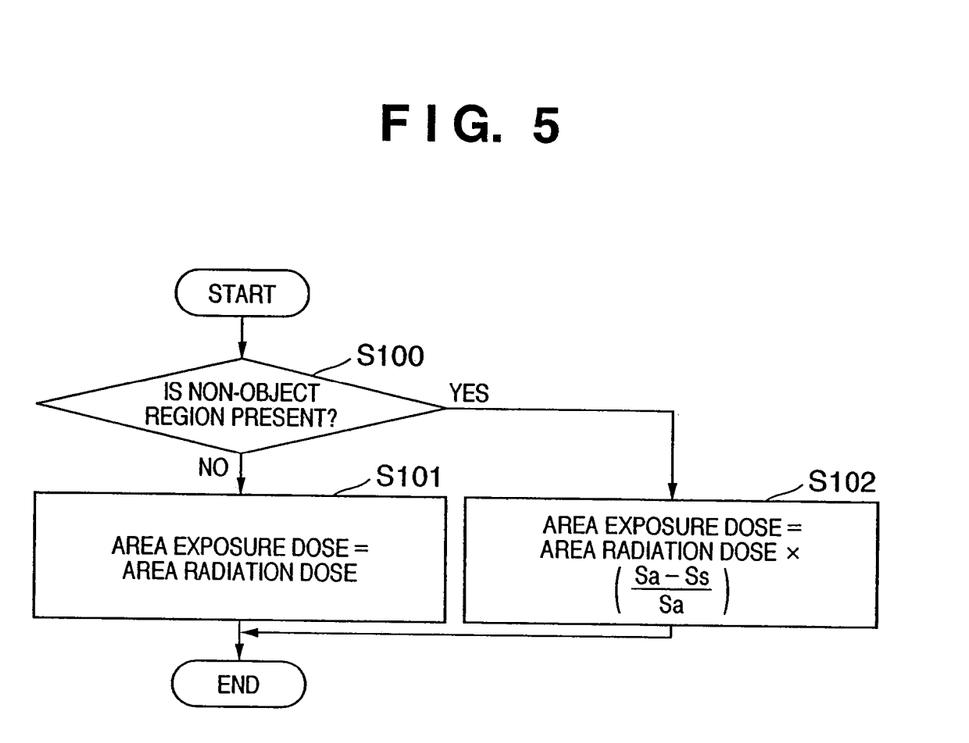
FIG. 5 is a flow chart showing a sequence for calculating an area exposure dose in step S5 in FIG. 4.

In the case shown in FIG. 5, the method of calculating an area exposure dose is changed depending on whether or not a non-object region is present. However, the present invention is not limited to this. Using always equation (1) will eliminate the necessity to change the calculation method depending on the presence/absence of a non-object region. This simplifies the processing.

In the first embodiment, an area exposure dose is calculated by calculating the area of a non-object region. However, an area exposure dose can also be calculated by recognizing a region which is not a non-object region (i.e., an object region) and calculating an area Se of the region. In this case, the following equation may be used in step S102 in FIG. 5:

$$\text{area exposure dose} = M*Se/Sa \quad (2)$$

As described above, according to the first embodiment, an area exposure dose can be properly acquired even in the presence of a non-object region.

The first embodiment has exemplified the case wherein the area dose value from the exit dosimeter 200 is used. However, a predictive value of an area radiation dose based on emission conditions (a tube current, tube voltage, emission time, and the like) for the X-ray generator may be used instead.

This embodiment and embodiments to be described later are based on the premise that the radiation field stop is stopped down to substantially limit the X-ray radiation field within the sensor region (the X-ray image detectable region in the sensor 11). Assume, however, that the X-ray radiation field is not limited within the sensor region. In this case, of the area dose M measured by the exit dosimeter 200 or the area dose predicted on the basis of the emission conditions, the dose (also called the effective dose or effective area dose) of X-rays which have reached the sensor must be calculated on the basis of the positional relationship between the X-ray radiation field and the sensor region. This calculation can be formulated by those skilled in the art, as needed.

<Second Embodiment>

The second embodiment of the present invention will be described next.

In most medical examinations in Japan, only the front of the chest of a patient is radiographed. In this case, since the chin of the patient is rested and positioned on the upper side of the sensor unit, non-object regions always appear above the two shoulders.

An area exposure dose measuring method suitable for such a case, i.e., a case wherein a radiation digital image always includes non-object regions, will be described below. Assume that in the following case, a sensor sensitivity holding unit is calibrated in advance to allow calculation of an area exposure dose per unit area from the electric charge quantity generated per unit area by the sensor upon reception of X-rays.

Figure 6:
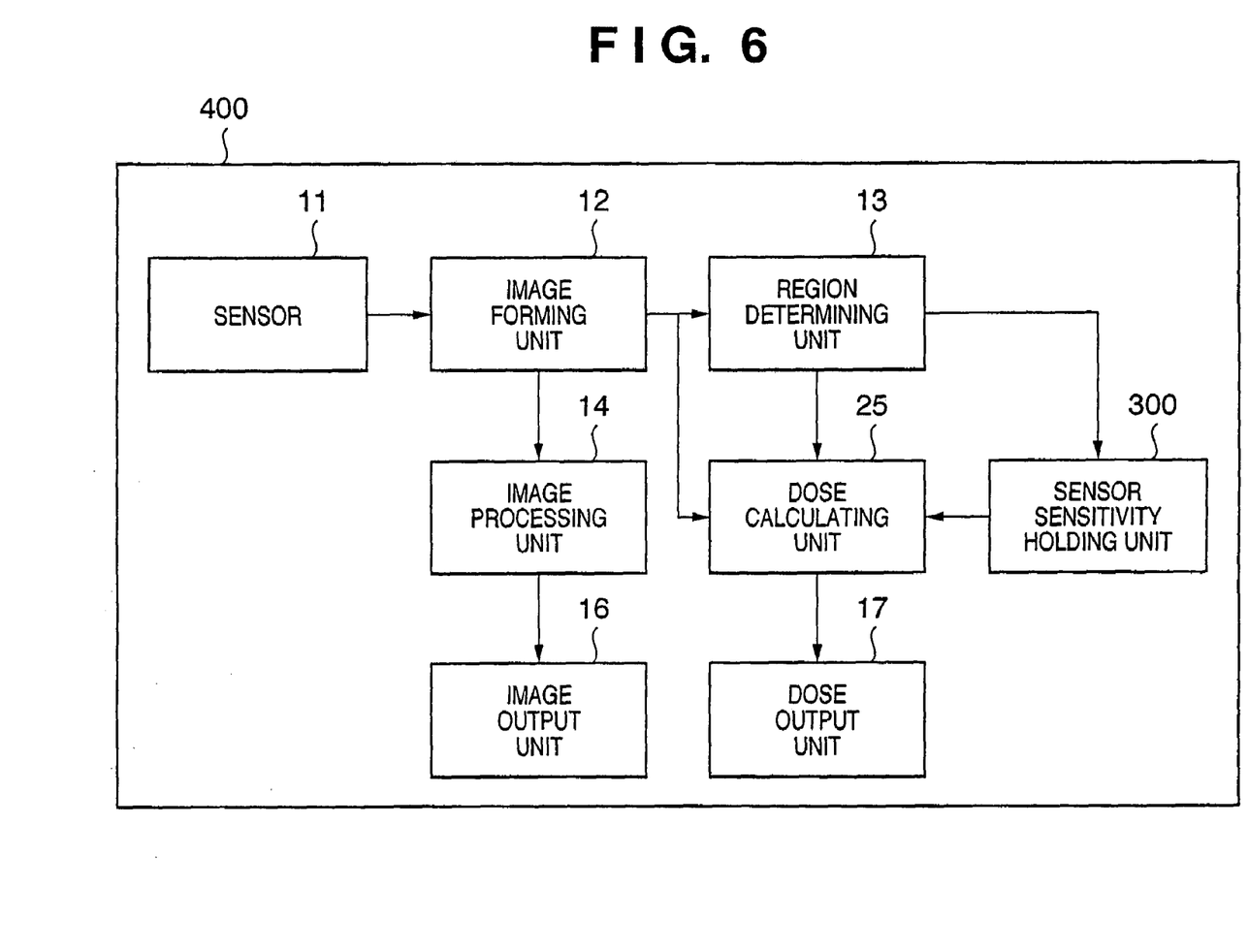
FIG. 6 is a block diagram showing the arrangement of an area exposure dosimetry system according to a second embodiment of the present invention.

FIG. 6 is a block diagram showing the arrangement of an exposure dosimetry system according to the second embodiment of the present invention. The arrangement of the exposure dosimetry system according to the second embodiment differs from that shown in FIG. 1 in that the system does not include the exit dosimeter 200, and a sensor sensitivity holding unit 300 is added to a digital radiography system. The same reference numerals as in FIG. 1 denote the same parts in FIG. 6, and a description thereof will be omitted.

Referring to FIG. 6, reference numeral 400 denotes a digital radiography system; and 300, the sensor sensitivity holding unit which holds the sensitivity of a sensor 11. The sensor sensitivity holding unit 300 holds an area dose conversion coefficient k for conversion of an electric charge quantity per unit area generated by the sensor upon reception of X-rays into an area exposure dose of X-rays per unit area which are received by the sensor. The sensor sensitivity holding unit 300 acquires an electric charge quantity e per unit area of a non-object region from a region determining unit 13, and calculates an area exposure dose L (=k×e) per unit area of the non-object region from the acquired value. In the second embodiment, a dose calculating unit 25 calculates the area exposure dose of a patient by using the image obtained from an image forming unit 12, the information output from the region determining unit 13, and an area exposure dose L per unit area from the sensor sensitivity holding unit 300. Of the components of the digital radiography system 400, the region determining unit 13, an image processing unit 14, the dose calculating unit 25, an image output unit 16, a dose output unit 17, and the sensor sensitivity holding unit 300 may be implemented by using a general-purpose personal computer and the like.

An area exposure dose measuring method in a case wherein a non-object region always exists will be described below with reference to FIGS. 7 and 2. The second embodiment does not include the exit dosimeter 200 in FIG. 2 or does not use it even if it exists.

Figure 7:
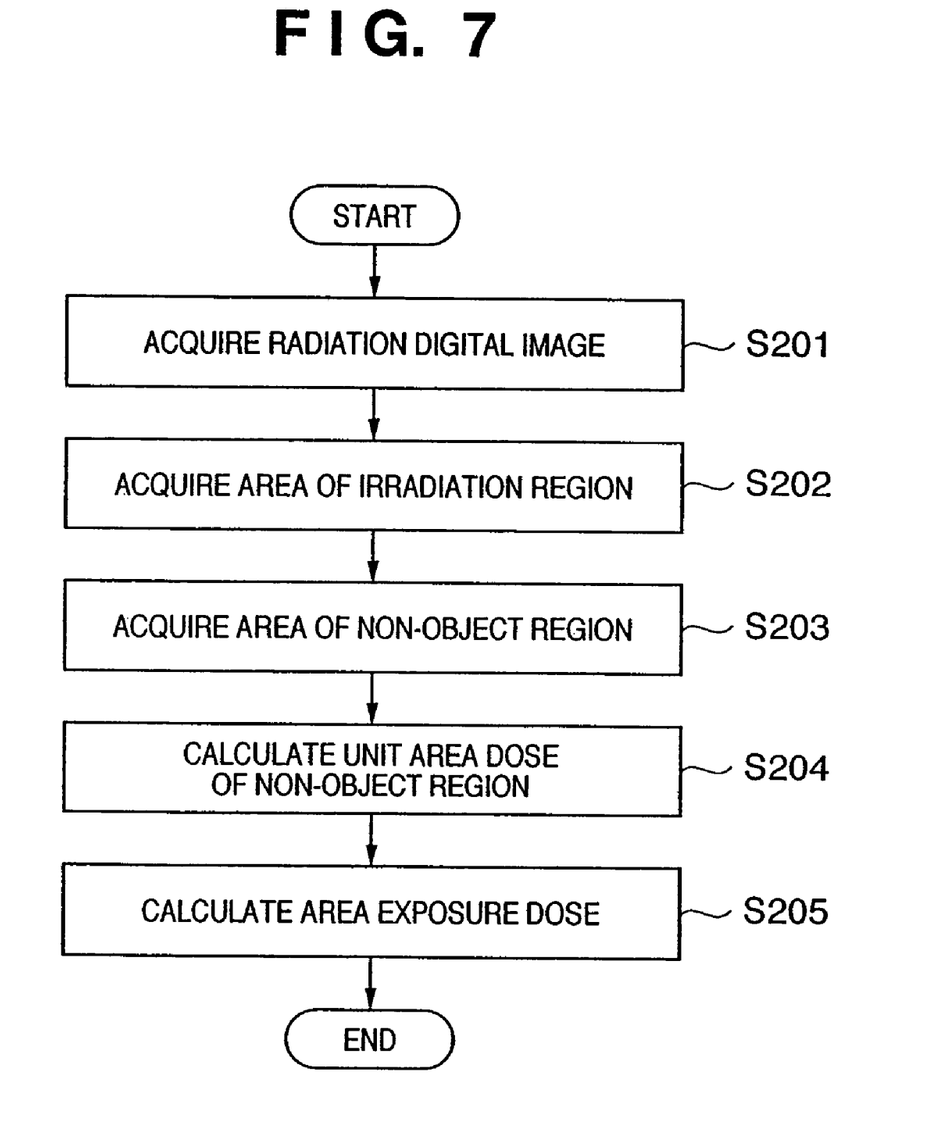
FIG. 7 is a flow chart showing the flow of processing for area exposure dose calculation according to the second embodiment of the present invention.

FIG. 7 is a flow chart showing the flow of processing for area exposure dose calculation in the second embodiment of the present invention. In step S201, after a human body 3 is irradiated with X-rays 4, the image forming unit 12 acquires data from the sensor 11 on an element (pixel) basis to form a radiation digital image. The region determining unit 13 then calculates an area Sa of an irradiation region on the basis of the information from the image forming unit 12 by the method described in the first embodiment with reference to FIG. 3 (step S202), and also calculates an area Ss of a non-object region (step S203). The sensor sensitivity holding unit 300 acquires an electric charge quantity per unit area of the non-object region from the region determining unit 13, and calculates an area exposure dose L per unit area of the non-object region from the acquired value (step S204). The dose calculating unit 25 calculates the exposure dose of the human body 3 from the area dose L per unit area of the non-object region, the area of the non-object region, and the area of the irradiation region (step S205). The dose calculating unit 25 calculates the exposure dose of the human body 3 by $$\text{area exposure dose} = L*(Sa-Ss) \quad (3)$$

As described above, according to the second embodiment, when there is a non-object region, a proper area exposure dose can be obtained without using any exit dosimeter. In addition, a digital radiography system can be provided at a low cost. Furthermore, there is no need to communicate emission conditions between the X-ray generator and the digital radiography system. Even if, therefore, emission conditions cannot be received from the X-ray generator because, for example, the X-ray generator has no available communication means, the digital radiography system can use the above method.

<Third Embodiment>

The third embodiment of the present invention will be described next. A method of calculating the area absorbed dose of a patient in the third embodiment will be described with reference to FIG. 8. The system arrangement of this embodiment is the same as that of the second embodiment described with reference to FIGS. 6 and 2 (this embodiment does not include the exit dosimeter 200 or does not use it like the second embodiment), and hence a description thereof will be omitted.

Figure 8:
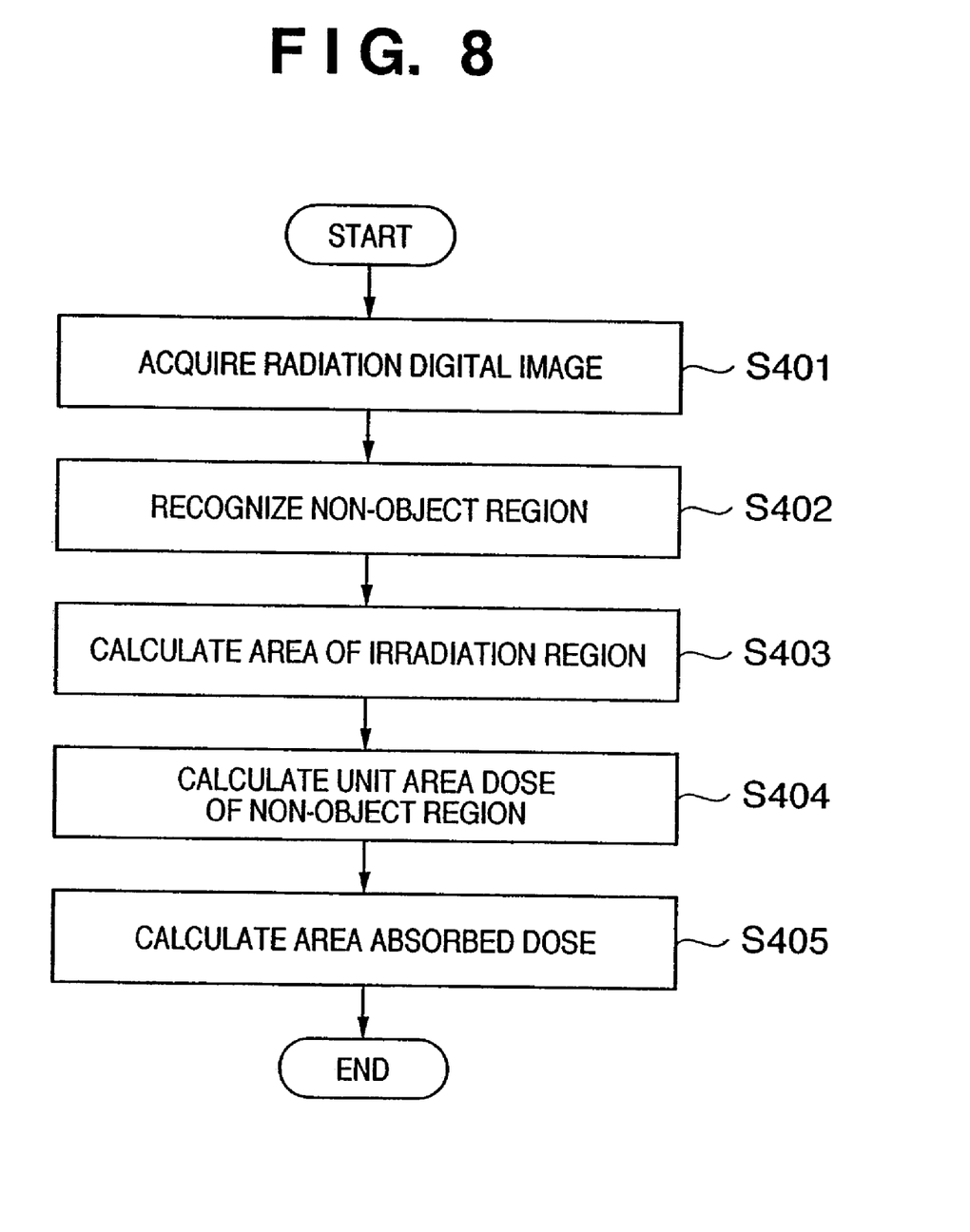
FIG. 8 is a flow chart showing a sequence for calculating an area absorbed dose according to a third embodiment of the present invention.

Referring to FIG. 8, after a human body 3 is irradiated with X-rays 4, an image forming unit 12 acquires data from a sensor 11 on an element (pixel) basis to form a radiation digital image (step S401). A region determining unit 13 discriminates a non-object region on the basis of the information from the image forming unit 12 (step S402). The region determining unit 13 also calculates an area Sa of an irradiation region (step S403). A dose calculating unit 25 acquires an electric charge quantity e per unit area of the non-object region and also acquires an area dose conversion coefficient k from a sensor sensitivity holding unit 300. The dose calculating unit 25 then calculates an area exposure dose L per unit area of the non-object region ($=k\times e$) (step S404). The dose calculating unit 25 further calculates the absorbed dose of the human body 3 from the area dose L per unit area of the non-object region, all the output values from the sensor 11, and the area Sa of the irradiation region (step S405). The dose calculating unit 25 calculates the area absorbed dose of the human body 3 by $$\text{area absorbed dose} = L \times Sa - \sum_{i=0}^{n} j(i) \quad (4)$$

where n is the number of pixels of the sensor, i is the ordinal number (position) of a pixel, and j(i) is the area dose of X-rays that have reached the ith pixel. Note that j(i) is also a function of the area dose conversion coefficient k, and is calculated by using the electric charge quantity of each pixel and the area dose conversion coefficient k.

The area absorbed dose measuring method will be described in detail next with reference to FIG. 9.

Figure 9:
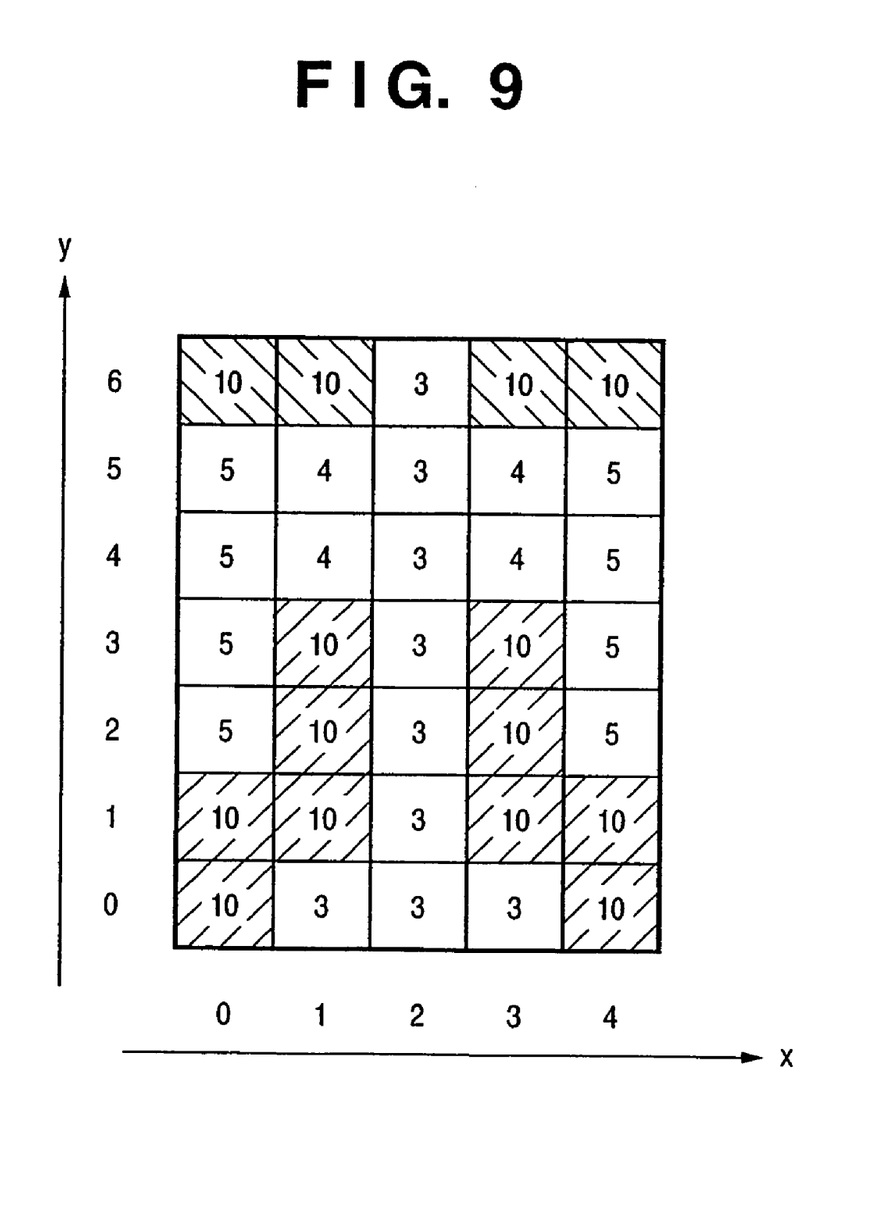
FIG. 9 is a schematic view showing signal values in a radiation digital image on a pixel basis according to the third embodiment of the present invention.

FIG. 9 is a schematic view showing a case wherein the image forming unit 12 formed an image by collecting electric charge quantities from the respective elements (pixels) of the sensor 11. Referring to FIG. 9, the respective pixels are partitioned with lines, and the numbers written on the respective pixels represent the area dose values of X-rays reaching the sensor 11, which are calculated on the basis of the acquired electric charge quantities. Note that the numerical values and the number of pixels in FIG. 9 are set for the sake of descriptive convenience, and different from actual numerical values and the actual number of pixels. The numbers shown outside the matrix are written along the x-axis and y-axis to specify each pixel. The third embodiment will be described on the assumption that one pixel corresponds to one unit area, and an X-ray field stop is so adjusted as to irradiate the entire surface of the sensor 11 with the X-rays 4.

In this case, according to the non-object region recognition method described above, the pixels in following coordinates indicate non-object regions. Note that the preceding numbers in the respective parentheses represent x-coordinates; and the succeeding numbers, y-coordinates:

(0, 6), (0, 1), (0, 0), (1, 6), (1, 3), (1, 2), (1, 1), (3, 6), (3, 3), (3, 2), (3, 1), (4, 6), (4, 1), (4, 0)

Since the area dose per unit area of all the pixels represented by these coordinates is 10, the area dose L per unit area of non-object regions is 10. In the third embodiment, since it is assumed that the irradiation region is equal to the sensor region and one pixel corresponds to a unit area, the area Sa of the irradiation region is equal to the number of sensor pixels, i.e., 35.

The sum of area doses of all the pixels is equal to the sum of all the numbers in the respective pixels in FIG. 9, which is calculated into 223.

Substituting these values into equation (4) yields the area absorbed dose of the human body as follows:

$$\text{area absorbed dose}=10\times35-223=127$$

As described above, according to the third embodiment, when there is a non-object region, a proper area absorbed dose can be obtained without using any exit dosimeter. In addition, a digital radiography system can be provided at a low cost. Furthermore, there is no need to communicate emission conditions between the X-ray generator and the digital radiography system. Even if, therefore, emission conditions cannot be received from the X-ray generator because, for example, the X-ray generator has no available communication means, the digital radiography system can use the above method.

<Fourth Embodiment>

The fourth embodiment of the present invention will be described below.

In the fourth embodiment, a method of accurately keeping the sensitivity of exposure/absorbed dosimetry by using an exit dosimeter and a digital radiography system will be described.

The second and third embodiments are based on the premise that a non-object region exists in a radiation digital image. When, however, the front of the chest and other regions are to be radiographed by using one digital radiography system, a radiation digital image including no non-object region may be imaged. In this case, area exposure dosimetry and area absorbed dosimetry are preferably performed by a combination of an exit dosimeter and a digital radiography apparatus or a combination of a predictive value of an area radiation dose based on the emission conditions for an X-ray generator and a digital radiography apparatus.

Figure 10:
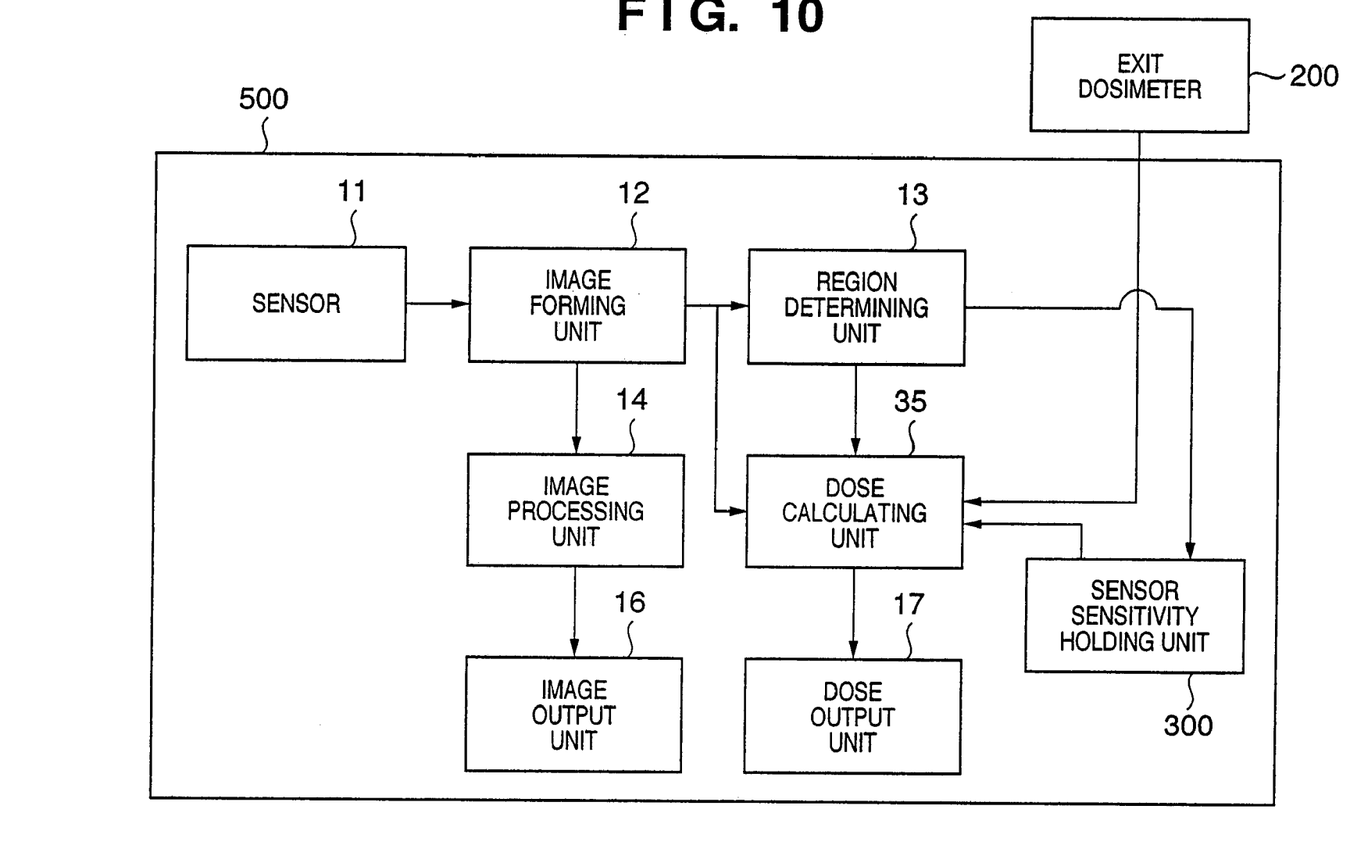
FIG. 10 is a block diagram showing the arrangement of an area absorbed dosimetry system according to a fourth embodiment of the present invention.

In the fourth embodiment, a method of quickly performing calibration with respect to changes over time in quality of the respective components of a measurement system like the one described above will be described. FIG. 10 is a block diagram showing the arrangement of an area absorbed dosimetry system according to the fourth embodiment. The arrangement of an area absorbed dosimetry system of the fourth embodiment differs from that shown in FIG. 6 in that it includes an exit dosimeter 200. The same reference numerals as in FIG. 1 denote the same parts in FIG. 10, and a description thereof will be omitted.

Referring to FIG. 10, reference numeral 500 denotes a digital radiography system; and 300, a sensor sensitivity holding unit which holds the sensitivity of a sensor 11. The sensor sensitivity holding unit 300 holds an area dose conversion coefficient k for conversion of an electric charge quantity per unit area generated by the sensor upon reception of X-rays into an area exposure dose of X-rays per unit area which are received by the sensor. The sensor sensitivity holding unit 300 acquires an electric charge quantity per unit area of a non-object region from a region determining unit 13, and calculates an area exposure dose L per unit area of the non-object region from the acquired value. The exit dosimeter 200 is placed on the side of the sensor with respect to an X-ray stop and nearer to the X-ray generator than an object. In the fourth embodiment, a dose calculating unit 35 calculates the area exposure dose of a patient by using the image obtained from an image forming unit 12, the information output from the region determining unit 13, the area exposure dose L per unit area from the sensor sensitivity holding unit 300, and the area dose value obtained from the exit dosimeter 200. Of the components of the digital radiography system 500, the region determining unit 13, an image processing unit 14, the dose calculating unit 35, an image output unit 16, a dose output unit 17, and the sensor sensitivity holding unit 300 may be implemented by using a general-purpose personal computer and the like.

Letting e be an electric charge quantity per unit area of a non-object region of the radiation digital image obtained by the digital radiography system 500, k be the area dose conversion coefficient of X-rays with respect to the electric charge quantity, Sa be the area of an irradiation region, and M be the area dose value acquired from the exit dosimeter 200, the following equation must hold for the combination of the exit dosimeter 200 and digital radiography system 500 shown in FIG. 10:

$$k = M/(e*Sa) \quad (5)$$

Figure 11:
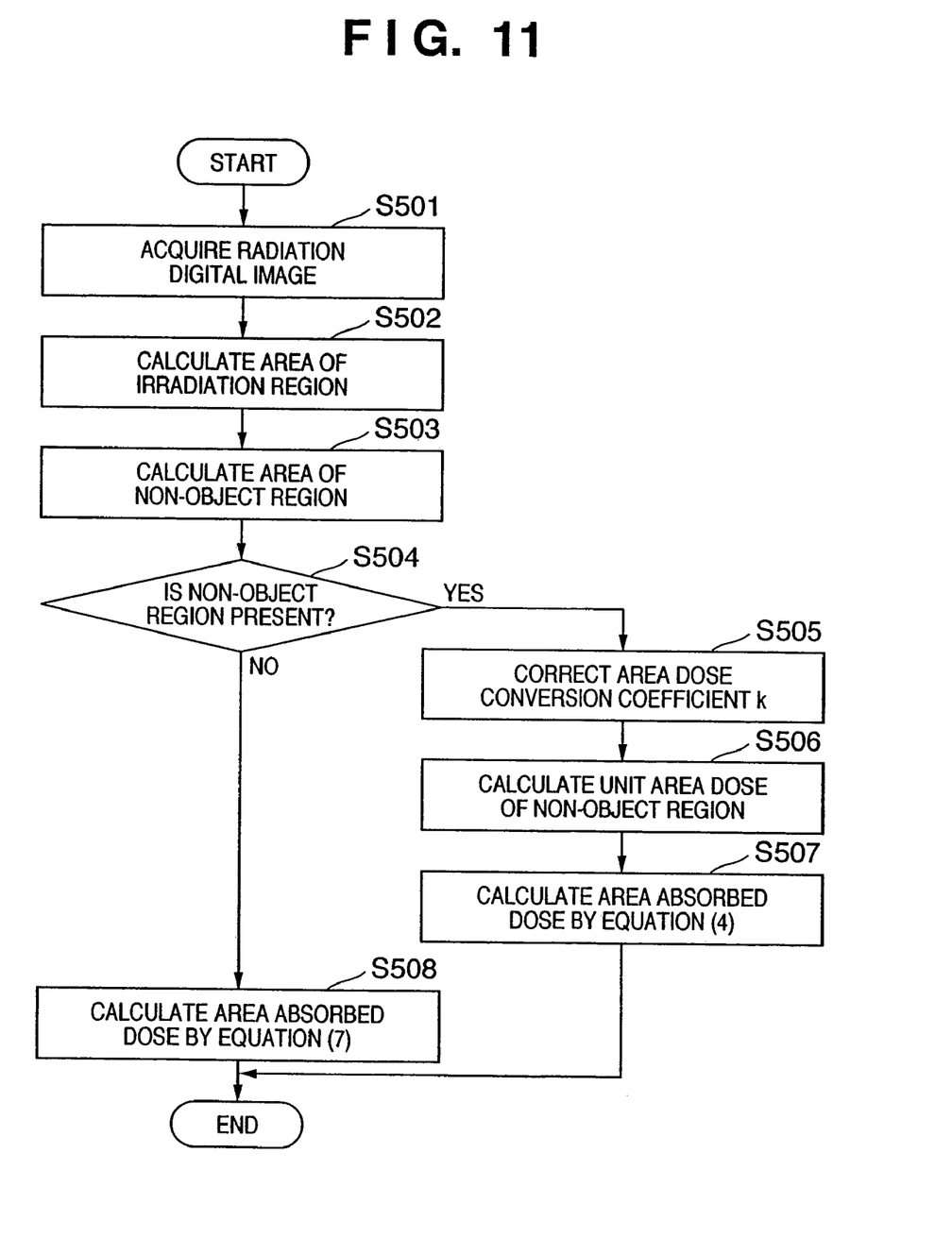
FIG. 11 is a flow chart showing a sequence for calculating an area absorbed dose calculation according to the fourth embodiment of the present invention.

A method of quickly calibrating the exposure dose measurement system will be described next with reference to equation (5) and FIGS. 10, 11, and 2. FIG. 11 is a flow chart showing a sequence for area absorbed dose calculation in the fourth embodiment of the present invention.

After a human body 3 is irradiated with X-rays 4, the image forming unit 12 acquires data from a-sensor 11 on an element (pixel) basis to form a radiation digital image (step S501). The region determining unit 13 calculates an area Sa of the irradiation region from the information output from the image forming unit 12 (step S502). The region determining unit 13 also calculates an area Ss of a non-object region (step S503). Next, the region determination unit 13 determines whether or not any non-object region is present (step S504). If no non-object region is present, the flow directly advances to step S508. If a non-object region is present, the area dose conversion coefficient K is obtained by substituting the area radiation dose M acquired from the exit dosimeter 200, the electric charge quantity e per unit area of the non-object region, and the area Sa of the irradiation region into equation (5), and the coefficient k in the sensor sensitivity holding unit 300 is replaced with the obtained coefficient K (step S505).

In step S506, the sensor sensitivity holding unit 300 acquires both the electric charge quantity e per unit area of the non-object region and the area dose conversion coefficient k from the sensor sensitivity holding unit 300, and calculates an area exposure dose L per unit area of the non-object region by using these values:

$$L = k*e \quad (6)$$

The dose calculating unit 35 calculates the absorbed dose of the human body 3 from the unit area dose L of the non-object region, output values from all the elements of the sensor 11, and the area Sa of the irradiation region (step 8507). Note that area absorbed dose calculation in step S507 is performed by using equation (4) used in the third embodiment:

$$\text{area absorbed dose} = L \times Sa - \sum_{i=0}^{n} j(i) \quad (4)$$

If no non-object region is present, the absorbed dose of the human body 3 is calculated in step S508 using the area radiation dose M acquired from the exit dosimeter 200 and the output values from all the elements of the sensor 11 according to equation (7):

$$\text{area absorbed dose} = M - \sum_{i=0}^{n-1} j(i) \quad (7)$$

In the case shown in FIG. 11, the method of calculating an area exposure dose is changed depending on whether or not a non-object region is present. However, the present invention is not limited to this. Using always equation (7) will eliminate the necessity to change the calculation method depending on the presence/absence of a non-object region. This simplifies the processing.

Since L and j(i) in equation (4) and j(i) in equation (7) are functions of the area dose conversion coefficient k, the coefficient k can be calibrated even in the presence of a non-object region in a radiation digital image in the above manner. Even if, therefore, the sensitivity of the sensor 11 changes over time, an area absorbed dose can be accurately and stably calculated.

In the fourth embodiment, the exit dosimeter 200 is used as a reference for the correction of the sensitivity of the sensor 11. If, however, the precision of the exit dosimeter 200 deteriorates over time, it is preferable to periodically calibrate the exit dosimeter 200. This makes it possible to build a system in which sensor sensitivity correction is properly executed.

The fourth embodiment has been described on the assumption that a change over time in the quality of the sensor is larger than that in the exit dosimeter 200. If a change over time in the quality of the exit dosimeter 200 is larger than that in the sensor, the sensitivity of the exit dosimeter 200 can be corrected, instead of sensor sensitivity, by using, for example, a communication means or the like for the exit dosimeter 200.

The fourth embodiment has exemplified the area absorbed dosimetry system. Obviously, however, the method of correcting the sensitivity of the sensor, and/or the exit dosimeter in this embodiment can also be effectively applied to an area exposure dosimetry system like the one described above.

In addition, the fourth embodiment has exemplified the case wherein the area dose conversion coefficient k is updated by using an area dose value from the exit dosimeter 200. However, an area radiation dose based on the emission conditions (a tube current, tube voltage, emission time, and the like) for the X-ray generator may be used. In this case, the sensitivity of the exit dosimeter 200 can also be corrected easily.

As described above, according to the fourth embodiment, since the area dose conversion coefficient k is automatically updated (calibrated) on the basis of an area dose value from the exit dosimeter, only the exit dosimeter is required to be calibrated. This saves labor and cost.

<Fifth Embodiment>

In the second, third, and fourth embodiments, the area dose conversion coefficient k is used as the sensitivity of the sensor 11. In some cases, however, the area radiation dose of X-rays on the sensor 11 and the electric charge quantity generated by the sensor 11 do not have a linear relationship, and a calibration cannot be done by using a single coefficient. In such a case, the relationship between the electric charge quantity generated by the sensor and the area radiation dose of X-rays may be specified by a nonlinear function representing the relationship, a reference table, or the like.

<Other Embodiment>

Each embodiment described above has exemplified the case wherein a digital X-ray sensor is used. However, the present invention is not limited to this. For example, in conventional film imaging, an accurate area exposure dose or area absorbed dose can be calculated by acquiring a digital image from a film through a film scanner or the like and applying the idea of the present invention to the digital image.

In each embodiment described above, X-ray radiation is used as a measurement target for an area exposure dose or area absorbed dose. However, another kind of radiation may be used.

Further, the present invention can be applied to a system constituted by a plurality of devices or to an apparatus comprising a single device.

Further, the object of the present invention can also be achieved by providing a storage medium storing program codes for performing the aforesaid processes to a computer system or apparatus (e.g., a personal computer), reading the program codes, by a CPU or MPU of the computer system or apparatus, from the storage medium, then executing the program.

In this case, the program codes read from the storage medium realize the functions according to the embodiments, and the storage medium storing the program codes constitutes the invention.

Further, the storage medium, such as a floppy disk, a hard disk, an optical disk, a magneto-optical disk, CD-ROM, CD-R, a magnetic tape, a non-volatile type memory card, and ROM, and computer network, such as LAN (local area network) and WAN (wide area network), can be used for providing the program codes.

Furthermore, besides aforesaid functions according to the above embodiments are realized by executing the program codes which are read by a computer, the present invention includes a case where an OS (operating system) or the like working on the computer performs a part or entire processes in accordance with designations of the program codes and realizes functions according to the above embodiments.

Furthermore, the present invention also includes a case where, after the program codes read from the storage medium are written in a function expansion card which is inserted into the computer or in a memory provided in a function expansion unit which is connected to the computer, CPU or the like contained in the function expansion card or unit performs a part or entire process in accordance with designations of the program codes and realizes functions of the above embodiments.

In a case where the present invention is applied to the aforesaid storage medium, the storage medium stores program codes corresponding to the flowchart of FIG. 5, 7, 8 or 11 described in the embodiments.

The present invention is not limited to the above embodiments and various changes and modifications can be made within the spirit and scope of the present invention. Therefore to apprise the public of the scope of the present invention, the following claims are made.

What is claimed is:

1. An area exposure dosimetry method comprising:
   acquiring a radiation image obtained by radiographing an object;
   detecting points in the radiation image where change in signal levels of the radiation image is higher than a predetermined threshold;
   connecting the detected points to make a contour;
   calculating at least one of an area of an object region and an area of a non-object region in the radiation image in accordance with the contour;
   acquiring an effective dose of radiation from a radiation generator; and
   calculating an area exposure dose as a radiation dose of the object on the basis of an area of the irradiation region in the radiation image, the calculated one of the area of the object region and the area of the non-object region, and the effective dose.

2. The method according to claim 1, wherein said calculating areas includes recognizing the irradiation region, and at least one of the object region and the non-object region in the radiation image.

3. The method according to claim 1, wherein in said calculating dose, letting M be the effective dose, Sa be the area of the irradiation region, Se be the area of the object region, and Ss be the area of the non-object region, the area exposure dose is calculated by one of M×Se/Sa and M×(Sa−Ss)/Sa.

4. The method according to claim 1, wherein in said calculating, if the non-object is not present, the effective dose acquired in the acquiring step is set as the area exposure dose.

5. The method according to claim 1, wherein in said acquiring, the effective dose is acquired from an area dosimeter provided in the radiation generator.

6. The method according to claim 1, wherein in said acquiring, the effective dose is calculated from a radiation generation condition for the radiation generator.

7. A storage medium readable by a data processing apparatus, said storage storing a program which is executable by the data processing apparatus and comprises program codes realizing the area exposure dosimtery method described in claim 1.

8. An area exposure dosimetry apparatus comprising:

an acquisition unit that acquires a radiation image obtained by radiographing an object;

a region determining unit that detects points in the radiation image where change in signal levels of the radiation image is higher than a predetermined threshold and connects the detected points to make a contour, and calculates at least one of an area of an object region and an area of a non-object region in the radiation image in accordance with the contour made by said region determining unit;

an acquisition unit that acquires an effective dose of radiation from a radiation generator; and a dose calculating unit that calculates an area exposure dose as a radiation dose of the object on the basis of an area of the irradiation region in the radiation image, the calculated one of the area of the object region and the area of the non-object region, and the effective dose.

* * * * *